United States Patent
Ladel et al.

(10) Patent No.: US 9,889,179 B2
(45) Date of Patent: Feb. 13, 2018

(54) FGF-18 COMPOUND DOSING REGIMEN

(71) Applicant: MERCK PATENT GMBH, Darmstadt (DE)

(72) Inventors: Christoph H. Ladel, Darmstadt (DE); Hans Guehring, Eltville (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/120,131

(22) PCT Filed: Feb. 20, 2015

(86) PCT No.: PCT/EP2015/053624
§ 371 (c)(1),
(2) Date: Aug. 19, 2016

(87) PCT Pub. No.: WO2015/124727
PCT Pub. Date: Aug. 27, 2015

(65) Prior Publication Data
US 2017/0072017 A1    Mar. 16, 2017

(30) Foreign Application Priority Data
Feb. 20, 2014  (EP) .................................. 14000600

(51) Int. Cl.
| | |
|---|---|
| *A61K 38/18* | (2006.01) |
| *A61K 31/196* | (2006.01) |
| *A61K 38/20* | (2006.01) |
| *A61K 9/00* | (2006.01) |
| *A61K 45/06* | (2006.01) |
| *A61K 38/16* | (2006.01) |

(52) U.S. Cl.
CPC ........ *A61K 38/1825* (2013.01); *A61K 9/0019* (2013.01); *A61K 31/196* (2013.01); *A61K 38/16* (2013.01); *A61K 38/2006* (2013.01); *A61K 45/06* (2013.01)

(58) Field of Classification Search
None
See application file for complete search history.

(56) References Cited

U.S. PATENT DOCUMENTS 8,207,115 B2    6/2012 Gimona et al.

FOREIGN PATENT DOCUMENTS

| WO | WO 2008/023063 | 2/2008 |
| WO | WO 2015/124731 | 8/2015 |
| WO | WO 2015/124735 | 8/2015 |
| WO | WO 2015/124739 | 8/2015 |

OTHER PUBLICATIONS

Ellsworth, J.L. et al. "Fibroblast growth factor-18 is a trophic factor for mature chondrocytes and their progenitors" *Osteoarthritis and Cartilage*, Apr. 1, 2002, pp. 308-320, vol. 10, No. 4.
Lohmander, L.S. et al. "Intraarticular Sprifermin (Recombinant Human Fibroblast Growth Factor 18) in Knee Osteoarthritis: A Randomized, Double-Blind, Placebo-Controlled Trial" *Arthritis & Rheumatology*, Jul. 2014, pp. 1820-1831, vol. 66, No. 7.
Power, J. et al. "Intra-Articular Injection of rhFGF-18 Improves the Healing in Microfracture Treated Chondral Defects in an Ovine Model" *Journal of Orthopaedic Research*, Jan. 16, 2014, pp. 669-676, vol. 32, No. 5.
Shimoaka, T. et al. "Regulation of Osteoblast, Chondrocyte, and Osteoclast Functions by Fibroblast Growth Factor (FGF)-18 in Comparison with FGF-2 and FGF-10" *The Journal of Biological Chemistry*, Mar. 1, 2002, pp. 7493-7500, vol. 277, No. 9.
Written Opinion in International Application No. PCT/EP2015/053624, dated Jun. 1, 2015, pp. 1-7.
Chevalier, X. et al. "Intraarticular Injection of Anakinra in Osteoarthritis of the Knee: A Multicenter, Randomized, Double-Blind, Placebo-Controlled Study" *Arthritis & Rheumatism*, Mar. 15, 2009, pp. 344-352, vol. 61, No. 3.
Evans, C. H. et al. "Progress in intra-articular therapy" *Nat. Rev. Rheumatol.*, Jan. 2014, pp. 11-22, vol. 10.

*Primary Examiner* — David Romeo
(74) *Attorney, Agent, or Firm* — Saliwanchik, Lloyd & Eisenschenk

(57) ABSTRACT

The present invention provides a new dosing regimen for administration of FGF-18 in the treatment of a cartilage disorder, such as osteoarthritis or cartilage injury. Specifically provided is a preferred treatment scheme comprising administrations every 3 weeks, 4 weeks or 5 weeks of an FGF-18 compound per treatment cycle. The new dosing regimen can include the co-adminsitration of an anti-inflammatory drug.

21 Claims, 8 Drawing Sheets

FGF-18 COMPOUND DOSING REGIMEN

CROSS-REFERENCE TO RELATED APPLICATION

This application is the U.S. national stage application of International Patent Application No. PCT/EP2015/053624, filed Feb. 20, 2015.

FIELD OF INVENTION

The present invention relates to the treatment of cartilage and cartilage/bone disorders, osteoarthritis and cartilage injury in particular. More particularly, it relates to an FGF-18 compound for use according to particular treatment regimens. Specifically, it provides treatment schemes comprising administrations every 3 weeks, 4 weeks or 5 weeks of an FGF-18 compound per treatment cycle. The dosing regimen can further comprise the administration of an anti-inflammatory drug with effects on symptoms (pain and function), such as anakinra or diclofenac.

BACKGROUND OF THE INVENTION

Cartilage is composed of chondrocytes (cells derived from mesenchymal cells) which are dispersed in the matrix (a firm, gel-like ground substance). The cartilaginous matrix is produced by these cells and comprises mainly Type II collagen fibers (except fibrocartilage which also contains Type I collagen fibers), proteoglycans, and elastin fibers. Cartilage is found, among other places, in the joints, the ribcage, the ears, the nose, the throat, the trachea and the intervertebral disks. There are three main types of cartilage, hyaline, elastic and fibrocartilage, providing notably different functional properties according to their histological morphology. Articular cartilage, for instance, is a hyaline cartilage, having viscoelastic properties, covering the articular surfaces of bones. The main purpose of articular cartilage is to provide smooth surfaces in order to ensure nearly frictionless movement of articulating bones.

Cartilage disorders broadly refers to diseases characterized by degeneration/disintegration of cartilage and abnormalities in the connective tissues which are manifested by inflammation, pain, stiffness and limitation of motion of the affected body parts. These disorders can be due to a pathology or can be the result of trauma or injury. Mature cartilage has very limited ability to self-repair, notably because mature chondrocytes have little potential for proliferation due to limited supply with nutrients linked to the absence of blood vessels in cartilage. Replacement of damaged cartilage, in particular articular cartilage, caused either by injury or disease, is a major challenge for physicians, and available surgical treatment procedures are considered unpredictable and effective for only a limited time in younger patients without osteoarthritic changes. Therefore, the majority of patients either do not seek treatment or are counseled to postpone treatment for as long as possible. When treatment is required, the standard procedure is age-dependent and varies between total or partial joint replacement, transplantation of pieces of cartilage or chondrocytes or marrow-stimulating techniques (such as microfracture). Microfracture is a cheap and common procedure that involves penetration of the subchondral bone to stimulate cartilage deposition by bone marrow-derived stem cells. However, it has been shown that this technique does not sufficiently repair the chondral defect and the new cartilage formed is mainly fibrocartilage, resulting in a short-lived repair tissue. Indeed, fibrocartilage does not have the same biomechanical properties as hyaline articular cartilage and often lacks proper lateral integration into the surrounding cartilage. For this reason, the newly synthesized fibrocartilage may break down more easily (expected time frame: 5-10 years).

For patients with osteoarthritis (OA) all these cartilage repair techniques fail. The remaining non-surgical treatment consists notably of physical therapy, lifestyle modification (e.g., body weight reduction), supportive devices, oral drugs (e.g., non-steroidal anti-inflammatory drugs), injection of drugs (e.g., hyaluronic acid and corticoids), and food suplementation. All these treatments are unable to stop OA disease progression. If the pain therapy also fails, surgery, such as joint replacement or high tibial osteotomy for the knee joint, is the remaining option for the patients. Tibial or femoral osteotomies (cutting the bone to rebalance joint wear) may reduce symptoms, help to maintain an active lifestyle, and delay the need for total joint replacement. Total joint replacement can provide relief for the symptoms of advanced osteoarthritis, but generally requires a significant change in a patient's lifestyle and/or activity level.

Current available drug treatments are mainly directed to pain relief. At this time, there is no commercially available treatment that restores the cartilage damage (Lotz, 2010).

Interleukin-1 alpha (IL-1α) and interleukin-1 beta (IL-1β) are naturally occurring agonists of the type I IL-1 receptor (IL-1RA). Overexpression of proinflammatory cytokines, such as IL-1, has been shown to play a major role in the pathogenesis of immunoinflammatory diseases such as rheumatoid arthritis (RA) (Bingham, 2002) or osteoarthritis (OA) (Lee et al., 2013). The clinical application of antagonizing IL-1α and IL-1β in RA has been investigated with anakinra (Kineret™), a recombinant, non-glycoslylated form of human IL-1ra. The use of this therapeutic protein has led to a reduction in frequency and severity of joint damage in RA patients (Bresnihan, 2002; St. Clair, 2002), as well as pain reduction (Mertens et al., 2009). This molecule has been approved in 2001 in the treatment of some types of RA. Although IL-1 is also involved in OA, anakinra therapy is not significantly associated with improvements in OA symptoms compared with placebo, although a tendency toward pain reduction with anakinra 150 mg versus placebo was noted (Chevalier et al., 2009).

Fibroblast Growth Factor 18 (FGF-18) is a member of the Fibroblast Growth Factor (FGF) family of proteins, closely related to FGF-8 and FGF-17. It has been shown that FGF-18 is a proliferative agent for chondrocytes and osteoblasts (Ellsworth et al., 2002; Shimoaka et al., 2002). FGF-18 has been proposed for the treatment of cartilage disorders such as osteoarthritis and cartilage injury, either alone (WO2008/023063) or in combination with hyaluronic acid (WO2004/032849).

Various dosing regimens have been suggested for FGF-18. For instance, Moore et al. (2005) disclosed administration twice weekly for 3 weeks, and WO2008/023063 taught administration once a week for 3 weeks. This last dosing regimen has been investigated in clinical trials (for more details see for instance NCT01033994, NCT00911469 and NCT01066871).

Although the dosing regimen described in WO2008/023063 gives good results in articular cartilage repair, there is still a risk of acute synovitis. For this reason, there is a need for a method of decreasing risk of treatment-related acute synovitis as well as increasing patient tolerance to intra-articular injection, while maintaining the efficacy for the treatment of cartilage disorders, notably via chondrocyte proliferation and subsequent cartilage repair. Such a method should not only allow articular cartilage repair, possibly in the absence of synovitis, but also allow reformation of new cartilage having good properties (i.e., mainly hyaline cartilage). Indeed, generation of said hyaline cartilage is valuable both as a therapeutic and as a component for biological matrices (Getgood et al., 2010). There is also a need for a method of decreasing pain/improving function, while maintaining the efficacy for the treatment of cartilage disorders. Indeed, pain is not only very often associated with cartilage disorders but represents the leading symptom for clinical detection of these disorders.

SUMMARY OF THE INVENTION

It is an object of the present invention to provide a method for treating a patient having a cartilage disorder comprising the administration of an FGF-18 compound, wherein the FGF-18 compound is administered at least two times per treatment cycle, said administrations being separated by about 3 to 5 weeks, preferably by a month (monthly administrations). In a preferred embodiment said administrations are separated by regular interval of about 3, 4 or 5 weeks each. Preferably, the FGF-18 compound is administered at regular intervals of once per month.

The present invention further provides an FGF-18 compound for use in the treatment of a patient having a cartilage disorder, wherein the FGF-18 compound is to be administered at least two times per treatment cycle, said administrations being separated by about 3 to 5 weeks, preferably by about one month (monthly administrations). In a preferred embodiment said administrations are separated by regular interval of about 3, 4 or 5 weeks each. Preferably, the FGF-18 compound is administered at regular intervals of once per month Preferably, the FGF-18 compound to be administered is the FGF-18 fragment designated herein as trFGF-18 (or sprifermin) and the posology cycle is 3 to 300 µg per intra-articular injection, once monthly for 3 consecutive months (one treatment cycle).

In the context on the present invention as a whole, any treatment (or any method for treating) with an FGF-18 compound can further comprise the administration of an anti-inflammatory drug with effects on symptoms (pain and function), such as anakinra or diclofenac. Preferably, such administration is performed at the same time as the administration of the FGF-18 compound. If an anti-inflammatory drug is needed, it would therefore follow that said anti-inflammatory drug is to be administered concomitantly with the FGF-18 compound at least two times per treatment cycle, said administrations being separated by about 3 to 5 weeks, preferably by about one month (monthly administrations). Preferably the anti-inflammatory drug is anakinra or diclofenac and the posology cycle is 0.01 to 500 mg per administration, once monthly for 3 consecutive months (one treatment cycle).

In a preferred embodiment such a treatment cycle (i.e., FGF-18 compound alone or in combination with an anti-inflammatory drug with effects on symptoms (pain and function)) may be repeated several months after the last injection of the preceding treatment cycle, for instance after 2, 4 or 6 months or even after 1 year.

In preferred embodiments of the invention, the cartilage disorder to be treated is arthritis, such as osteoarthritis, or cartilage injury with or without surgical intervention such as microfracture. It has surprisingly been found that the methods and uses of the present invention notably improve cartilage repair and stimulate proliferation of chondrocytes, and, in the meantime, increase patient tolerance to intra-articular injection. It has further surprisingly been found that when anakinra or diclofenac is used together with FGF-18, it is able to efficiently restore the proliferative activity of the FGF-18 compound. Another advantage of the present invention is that synovitis will be reduced compared to what is observed with other regimens.

DEFINITIONS

The term "FGF-18 compound" or "FGF-18", as used herein, is intended to be a protein maintaining at least one biological activity of the human FGF-18 protein. FGF-18 may be native, in its mature form, a recombinant form or a truncated form thereof. Biological activities of the human FGF-18 protein notably include the increase in chondrocyte or osteoblast proliferation (see WO98/16644) or cartilage formation (see WO2008/023063). Native, or wild-type, human FGF-18 is a protein expressed by chondrocytes of articular cartilage. Human FGF-18 was first designated zFGF-5 and is fully described in WO98/16644. SEQ ID NO: 1 corresponds to the amino acid sequence of the native human FGF-18, with a signal peptide consisting of amino acid residues 1(Met) to 27(Ala). The mature form of human FGF-18 corresponds to the amino acid sequence from residue 28(Glu) to residue 207(Ala) of SEQ ID NO: 1 (180 amino acids).

FGF-18, in the present invention, may be produced by a recombinant method, such as taught by WO2006/063362. Depending on the expression systems and conditions, FGF-18 in the present invention is expressed in a recombinant host cell with a starting Methionine (Met) residue or with a signal sequence for secretion. When expressed in a prokaryotic host, such as E. coli, FGF-18 contains an additional Met residue in the N-terminal of its sequence. For instance, the amino acid sequence of human FGF-18, when expressed in E. coli, starts with a Met residue in N-term (position 1) followed by residues 28(Glu) to residue 207(Ala) of SEQ ID NO: 1.

The term "truncated form of FGF-18", as used herein, refers to a protein which comprises or consists of residues 28(Glu) to 196(Lys) of SEQ ID NO: 1. Preferably, the truncated form of FGF-18 protein is the polypeptide designated "trFGF-18" (170 amino acids; also known as rhFGF-18 or sprifermin), which starts with a Met residue (in the N-terminal) followed by amino acid residues 28(Glu)-196 (Lys) of the wild-type human FGF-18. The amino acid sequence of trFGF-18 is shown in SEQ ID NO: 2 (amino acid residues 2 to 170 of SEQ ID NO: 2 correspond to amino acid residues 28 to 196 of SEQ ID NO: 1). trFGF-18 is a recombinant truncated form of human FGF-18, produced in E. coli (see WO2006/063362). trFGF-18 has been shown to display similar activities to the mature human FGF-18, e.g., it increases chondrocyte proliferation and cartilage deposition, leading to repair and reconstruction for a variety of cartilaginous tissues (see WO2008/023063).

The terms "anti-inflammatory drug with effects on symptoms (pain and function)" or "anti-inflammatory drug" as used herein refer to an anti-inflammatory drug having effects on symptoms linked to the cartilage disorders to be treated such as pain and function. The preferred anti-inflammatory drugs to be used according to this invention are anakinra and diclofenac. Anakinra is a recombinant, nonglycosylated form of human interleukin-1 receptor antagonist (IL-1Ra). It is commercialized under the name Kineret®. Its sequence corresponds to SEQ ID NO: 3. Diclofenac (i.e., 2-(2,6-dichloranilino) phenylacetic acid) is a drug well-known for reducing inflammation and as an analgesic reducing pain in certain conditions. It is commercialized under various trade names.

The term "about" in "about 3 to 5 weeks" or "about one month" encompasses administrations separated by 3 weeks (21 days) to 5 weeks (35 days) or by one month, as well as administrations separated by 3 to 5 weeks+/−a few days or by one month+/− a few days (e.g., +/−1, 2, 3, 4 day(s)). Indeed, it should be understood that, notably from a practical point of view, the administration of the FGF-18 compound, for instance trFGF-18, cannot always be performed at exact intervals, e.g., exactly 4 weeks (28 days) day per day after the previous administration. Therefore, in the context of the invention, 4 weeks means 28 days, but may also be 24, 25, 26, 27, 28, 29, 30, 31 or 32 days after the previous administration, for the convenience of the patient. In the context of the present invention, the term "4 weeks" is similar to the term "1 month" and they can be used interchangeably (FIG. 1). "4 weeks" will be preferably used should one refer to "days" (e.g. first injection on a Monday, following injection on a Monday 4 weeks after) and "month" will be preferably used should one refer to a "date" (e.g., first injection the $1^{st}$ of August, following injection the $1^{st}$ of September).

The term "treatment cycle" or "cycle" corresponds to the period wherein an FGF-compound is given every 3, 4 or 5 weeks or every month (consecutive administrations). As an example, a treatment cycle can consist of 3 injections at 3-week intervals or can consist of 3 injections at 4-week intervals. Such a "treatment cycle" can be repeated. For instance, a second "treatment cycle" can be performed 3, 4, 5 or 6 months after the last injection of the previous cycle. Alternatively, a second cycle can also be performed 1 year or 2 years after the first injection in the first cycle. As an example, a first treatment cycle consisting of 3 injections at 4-week intervals can be followed, 3 months after the last injection of said cycle, by a second treatment cycle of 3 injections at 4-week intervals.

The term "cartilage disorder", as used herein, encompasses disorders resulting from damage due to injury, such as traumatic injury, chondropathy or arthritis. Examples of cartilage disorders that may be treated by the administration of the FGF-18 formulation described herein include but are not restricted to arthritis, such as osteoarthritis, and cartilage injury. Degenerative diseases/disorders of the cartilage or joint, such as chondrocalcinosis, polychondritis, relapsing polychondritis, ankylosing spondylitis or costochondritis, are also encompassed by this wording. The International Cartilage Repair Society has proposed an arthroscopic grading system to assess the severity of the cartilage defect: grade 0: (normal) healthy cartilage, grade 1: the cartilage has a soft spot or blisters, grade 2: minor tears visible in the cartilage, grade 3: lesions have deep crevices (more than 50% of cartilage layer) and grade 4: the cartilage tear exposes the underlying (subchronal) bone (see ICRS publication: see Worldwide Website: cartilage.org/_files/content-management/ICRS_evaluation.pdf, page 13).

The term "arthritis" as used herein encompasses disorders such as osteoarthritis, rheumatoid arthritis, juvenile rheumatoid arthritis, infectious arthritis, psoriatic arthritis, Still's disease (onset of juvenile rheumatoid arthritis) or osteochondritis dissecans. It preferably includes diseases or disorders in which the cartilage is damaged.

The term "osteoarthritis", or "OA", is used to intend the most common form of arthritis. The term "osteoarthritis" encompasses both primary osteoarthritis and secondary osteoarthritis (see for instance The Merck Manual, $17^{th}$ edition, page 449). Osteoarthritis may be caused by the breakdown of cartilage. Bits of cartilage may break off and cause pain and swelling in the joint between bones. Over time, the cartilage may wear away entirely, and the bones will rub together. Osteoarthritis can affect any joint but usually concerns hands, shoulders and weight-bearing joints such as hips, knees, feet, and spine. In a preferred example, the osteoarthritis may be knee osteoarthritis or hip osteoarthritis. This wording notably encompasses the forms of osteoarthritis which are classified as stage 1 to stage 4 or grade 1 to grade 6 according to the OARSI classification system. The skilled person is fully aware of osteoarthritis classifications that are used in the art, in particular said OARSI assessment system (also named OOCHAS; see for instance Custers et al., 2007). Osteoarthritis is one of the preferred cartilage disorders that can be treated by administering the FGF-18 compounds according to the present invention.

The term "cartilage injury" as used herein is a cartilage disorder or cartilage damage resulting, notably, from trauma. Cartilage injuries can occur notably after traumatic mechanical destruction, notably further to an accident or surgery (for instance microfracture surgery). The term "cartilage injury" also includes chondral or osteochondral fracture and damage to the meniscus. Also considered within this definition is sport-related injury or sport-related wear of tissues of the joint. The term also includes microdamage or blunt trauma, a chondral fracture, an osteochondral fracture or damage to the meniscus.

In the context of the present invention, the "efficacy" of a treatment can be measured based on changes in the thickness of the cartilage, for instance the thickness of the articular cartilage of the joint. This thickness can be assessed, for instance, through X-ray computed tomography, Magnetic Resonance Imaging (MRI) or ultrasonic measurements.

DETAILED DESCRIPTION OF THE INVENTION

The present invention provides administration schemes for the treatment of various cartilage disorders, such as osteoarthritis and cartilage injury, with an FGF-18 compound. Preferably, said FGF-18 compound is trFGF-18 as defined above. In the context of the present invention it has been shown that FGF-18 compounds have optimal disease- or symptom-ameliorating effects on cartilage disorders when administered according to the methods and uses disclosed herein. It has been surprisingly found that the dosing regimens of the present invention (i.e., less frequent dosing schedules than once a week for three weeks per treatment cycle) cause reduced inflammation (e.g., acute synovitis) status during the next injection and therefore the full activity of FGF-18 compounds can be observed. This finding was not expected because of the rather short half-life of FGF-18 in the joint (less than 24 hours).

In the context of the present invention as a whole, any treatment (or any method for treating) with an FGF-18 compound can further comprise the administration of an anti-inflammatory drug with effects on symptoms (pain and function), such as anakinra or diclofenac. Preferably, such administration (or co-administration) is performed at the same time as (i.e., concomitantly with) the administration of the FGF-18 compound.

In one embodiment, the present invention provides a method for treating a patient having a cartilage disorder comprising the administration of an FGF-18 compound wherein the FGF-18 compound is administered at least two times per treatment cycle, said administrations being separated by about 3 to 5 weeks, preferably by about 1 month. The preferred FGF-18 compound is trFGF-18. In a preferred embodiment the FGF-18 compound is administered for 3 consecutive months per treatment cycle (i.e., 3 times per treatment cycle, at regular intervals of once per month or once every four weeks). Alternatively, the FGF-18 compound can be administered 3 times per treatment cycle, at regular intervals of 3 weeks or 5 weeks. Such treatment may comprise 1, 2 or 3 treatment cycles per year. An anti-inflammatory drug, such as anakinra or diclofenac, can be administered at the same time as the FGF-18 compound.

In another aspect of the present invention there is provided an FGF-18 compound for use in the treatment of a patient having a cartilage disorder, wherein the FGF-18 compound is administered at least two times per treatment cycle, said administrations being separated by about 3 to 5 weeks, preferably by about 1 month. The preferred FGF-18 compound is trFGF-18. In a preferred embodiment the FGF-18 compound is administered for 3 consecutive months per treatment cycle (i.e., 3 times per treatment cycle, at regular intervals of once per month or once every four weeks). Alternatively, the FGF-18 compound can be administered 3 times per treatment cycle, at regular intervals of 3 weeks or 5 weeks. Such treatment may comprise 1, 2 or 3 treatment cycles per year. An anti-inflammatory drug with effects on symptoms (pain and function), such as anakinra or diclofenac, can be administered at the same time as the FGF-18 compound.

According to the present invention, the administration of the FGF-18 compound, either alone or in combination with an anti-inflammatory drug, such as anakinra or diclofenac, is to be performed at regular intervals; however, slight variations of +/− a few days are authorized (preferably no more than 3 or 4 days). For example, where administrations are separated by about 4 weeks, if the first administration of a cycle is given on a Tuesday, the second administration may be made on the Tuesday 4 weeks after the first administration (regular interval) or a few days before or after (for instance the Monday before or Thursday after). Similarly, where administrations are separated by about 1 month, if the first administration is given for instance on the 1$^{st}$ of August, the second administration may be made on the 1$^{st}$ of September (a Thursday, for instance), i.e., one month after the first administration (regular interval) or a few days before or after (for instance the Monday, Tuesday or Wednesday before the 1$^{st}$ of September or the Friday or Monday following he 1$^{st}$ of September). Such flexibility allows the dosing regimen to be notably less restricting and more convenient for the patient.

Preferably, administrations are performed on a regular interval basis, e.g., every 3, 4 or 5 weeks or every month. In a particular embodiment, said administrations are separated by about 1 month (or about 4 weeks). In one preferred embodiment they are separated by 1 month or by 4 weeks (i.e., monthly injections). Preferably, the FGF-18 compound is to be administered at regular intervals once per month (or once every 4 weeks). Alternatively, the FGF-18 compound can be administered at regular intervals once every 3 weeks or once every 5 weeks.

In the context of the present invention as a whole, the FGF-18 compound is administered at least two times per treatment cycle. It can also be administered, for instance, at least 3 times or at least 4 times per treatment cycle. Preferably, it is administered 3 times or 4 times per treatment cycle.

In a preferred embodiment, the FGF-18 compound, either alone or in combination with an anti-inflammatory drug (such as anakinra or diclofenac), is to be administered for at least 2 consecutive months, at least 3 consecutive months or at least 4 consecutive months per treatment cycle. In a further preferred embodiment the FGF-18 compound, either alone or in combination with an anti-inflammatory drug (such as anakinra or diclofenac), is administered for 2 consecutive months, 3 consecutive months or 4 consecutive months per treatment cycle. In an even preferred embodiment, it is administered for 3 consecutive months.

In the context of the present invention as a whole, such treatment may comprise several treatment cycles per year, such as 1, 2 or 3 treatment cycles per year. In one preferred embodiment, such treatment comprises 2 cycles per year. As an alternative, the treatment comprises 1 cycle per year, repeated 1 year or 2 years after the beginning of the first treatment cycle. As an example, should a treatment comprise 1 cycle, said treatment may consist of 3 injections at 3-week intervals or may consist of 3 injections at 4-week intervals. As a further example, should a treatment comprise at least 2 cycles, a first treatment cycle consisting of 3 injections at 3-week intervals can be followed, several months after the last injection of said cycle, by a second treatment cycle of 3 injections at 3-week intervals; or a first treatment cycle consisting of 3 injections at 4-week intervals can be followed, several months after the last injection of said cycle, by a second treatment cycle of 3 injections at 4-week intervals.

The FGF-18 compound of the invention is preferably selected from the group consisting of a) a polypeptide comprising or consisting of the human FGF-18 mature form comprising residues 28-207 of SEQ ID NO: 1, or b) a polypeptide comprising or consisting of FGF-18 (170AA) (SEQ ID NO: 2). Particularly, this compound is selected from human wild-type mature FGF-18 or trFGF-18. Said compound increases cartilage deposition and allows cartilage repair.

In a further preferred embodiment, the treatment comprises administration of the FGF-18 compound at a dose of 3-600 micrograms (μg or mcg), or preferably 3-300 μg, or preferably 10-200 μg, or more preferably 30-150 μg, or even more preferably 30-120 μg per single intra-articular administration. In a preferred embodiment the treatment comprises administration at a dose of about 3, 10, 20, 30, 40, 50, 60, 90, 100, 120, 150, 180, 200, 240 or 300 μg per single intra-articular administration of the FGF-18 compound. Preferred doses include 10, 20, 30, 60, 90, 120, 180, 240 or 300 μg per single intra-articular administration of the FGF-18 compound. It should be understood that the dose of the FGF-18 compound to be administered will be different if the patient to be treated is a human or a non-human mammal. For instance, for dogs, the dose will be preferably 5-fold less important than for humans. As an example, should the human dose range from 30 to 120 μg per single intra-articular administration, the dose for a dog could range from 5 to 20 μg per single intra-articular administration. Examples of dosing for rats and rabbits can be found in the Examples section.

In the context of the present invention as a whole, the FGF-18 compound can be used in combination with an anti-inflammatory drug with effects on symptoms (pain and function). The preferred anti-inflammatory drug is anakinra (see SEQ ID NO: 3) or diclofenac. When any one of anakinra or diclofenac is administered, the treatment comprises administration at a dose of 0.01-500 milligrams (mg), preferably 0.1-250 mg, or more preferably 0.5-150 mg per single administration, either intra-articularly (the preferable way for anakinra, for instance) or orally (the preferable way for diclofenac, for instance). In a preferred embodiment the treatment comprises administration at a dose of about 0.03, 0.1, 0.25, 0.3, 0.5, 1, 1.5, 2, 5, 10, 15, 20, 30, 40, 50, 60, 70, 80, 90, 100, 150, 200, 250 or 300 mg per single administration of the anti-inflammatory drug. Preferred doses include 0.5, 1, 5, 1.5, 10, 50, 100 and 150 mg per single administration. It should be understood that the dose of anti-inflammatory drug to be administered will be different if the patient to be treated is a human or a non-human mammal. For instance, for dogs, the dose will be preferably 6-fold less than for humans. As an example, if the human dose of anakinra is 150 mg per single intra-articular administration, the dose for a dog could be 25 mg per single intra-articular administration. The physician will adapt the dosing regimen for the anti-inflammatory drug case by case, depending on the patient and the anti-inflammatory drug to be administered. For instance, for diclofenac given orally, the dosing regimen can be 50 or 75 mg, two or three times a day.

FGF-18 compounds may be formulated as a pharmaceutical composition, i.e., together with a pharmaceutically acceptable carrier, excipient or the like. The definition of "pharmaceutically acceptable" is meant to encompass any carrier, excipient or the like which does not interfere with the effectiveness of the biological activity of the active ingredient and that is not toxic to the patient to which it is administered. For example, for parenteral administration, the active protein(s) may be formulated in a unit dosage form for injection in vehicles such as saline, dextrose solution, serum albumin and Ringer's solution. Formulations for intra-articular application will comply with most of the requirements that also apply to other injection formulations, i.e., they need to be sterile and compatible with the physiological conditions at the application site (e.g., knee joint, synovial fluid). The excipients used for intra-articular injection may also be present in other injection formulations, e.g., for intramuscular or subcutaneous application. Such formulations of FGF-18 compounds, including at least one further pharmaceutically acceptable carrier, excipient or the like, are herein also referred to as "FGF-18 compositions" or "FGF-18 formulations". Said "FGF-18 compositions" or "FGF-18 formulations" are also useful in the context of the present invention.

If an anti-inflammatory drug, such as anakinra or diclofenac, is used together with an FGF-18 compound, it can either be added to the FGF-18 compound formulation before administration, or co-administered, either using 2 different syringes/needles, or using 2 different syringes but preferably the same needle to increase patient convenience. Alternatively, the anti-inflammatory drug can be administered orally or by any other way of administering.

FGF-18 compounds, such as trFGF-18, and compositions containing FGF-18 compounds ("FGF-18 compositions") will be useful for treating cartilage disorders. In particular it can be useful for treating articular cartilage defects in synovial joints that are, for instance, due to superficial fibrillation (early osteoarthritis), cartilage degeneration due to osteoarthritis, and chondral or osteochondral defects due to injury or disease. FGF-18 compounds and compositions may also be useful for treating joint disease caused by osteochondritis dissecans and degenerative joint diseases. In the field of reconstructive and plastic surgery, FGF-18 compounds and compositions will be useful for autogenous or allogenic cartilage expansion and transfer for reconstruction of extensive tissue defects. FGF-18 compositions can be used to repair cartilage damage in conjunction with lavage of the joint, stimulation of bone marrow, abrasion arthroplasty, subchondral drilling, or microfracture of the subchondral bone. The optional co-administration with an anti-inflammatory drug with effects on symptoms (pain and function), such as anakinra or diclofenac, would decrease pain associated with the cartilage disorder to be treated.

In a preferred embodiment, the cartilage disorder to be treated according to the invention is osteoarthritis, such as knee osteoarthritis or hip osteoarthritis. The osteoarthritis to be treated can be, for example, and not limited to, primary osteoarthritis or secondary osteoarthritis, as well as osteoarthritis which is classified as stage 1 to stage 4 or grade 1 to grade 6 according to the OARSI classification system.

In another preferred embodiment, the cartilage disorder to be treated according to the invention is cartilage injury with and without surgical interventions, such as microfractures. Additionally, after the growth of cartilage due to the administration of the FGF-18 composition (administered either alone or together with an anti-inflammatory drug, such as anakinra or diclofenac), a surgical treatment may be necessary to suitably contour the newly formed cartilage surface.

In a preferred embodiment, the treatment comprises intra-articular administration of the FGF-18 compound or FGF-18 composition, either alone or together with an anti-inflammatory drug with effects on symptoms (pain and function), such as anakinra or diclofenac. FGF-18 compounds or FGF-18 compositions can be applied, either alone or together with an anti-inflammatory drug, such as anakinra or diclofenac, by direct injection into the synovial fluid of the joint or directly into the defect, either alone or complexed with a suitable carrier for extended release of protein (e.g., sustained-release formulations) or restricted local release. Preferably, the mode of administration of the FGF-18 compound, either alone or together with an anti-inflammatory drug, such as anakinra or diclofenac, described herein is selected from the group consisting of peri-synovial administration, intra-synovial administration, peri-articular administration and intra-articular administration. In a preferred embodiment, the FGF-18 compound described herein is administered, either alone or together with an anti-inflammatory drug, such as anakinra or diclofenac, preferably intra-articularly (administration within a joint). The anti-inflammatory drug is administered preferably intra-articularly (the preferable way for anakinra) or orally (the preferable way for diclofenac). The intra-articular administration is done in a joint selected from the joint of the hip, knee, elbow, wrist, ankle, spine, foot, finger, toe, hand, shoulder, rib, shoulder blade, thigh, shin, heel and along the bony points of the spine. In yet another preferred embodiment the intra-articular administration is done in a joint of the hip or the knee.

DESCRIPTION OF THE FIGURES

FIG. 1A: once weekly dosing regimen; FIG. 1B: once monthly (or every 4 weeks) dosing regimen; FIG. 1C: once monthly (or every 4 weeks) dosing regimen+/−a few days of variation accepted for the convenience of the patient.

DESCRIPTION OF THE SEQUENCES

Figure 1A:
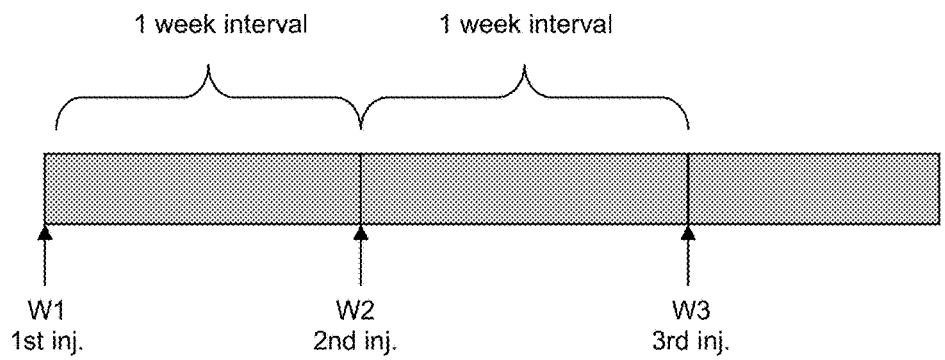
FIGS. 1A-1C: Treatment schedule outline.
Figure 1B:
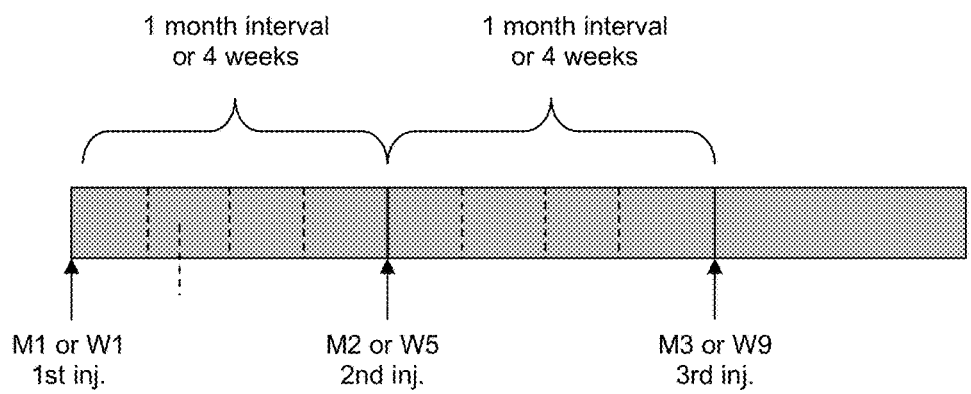
Figure 1C:
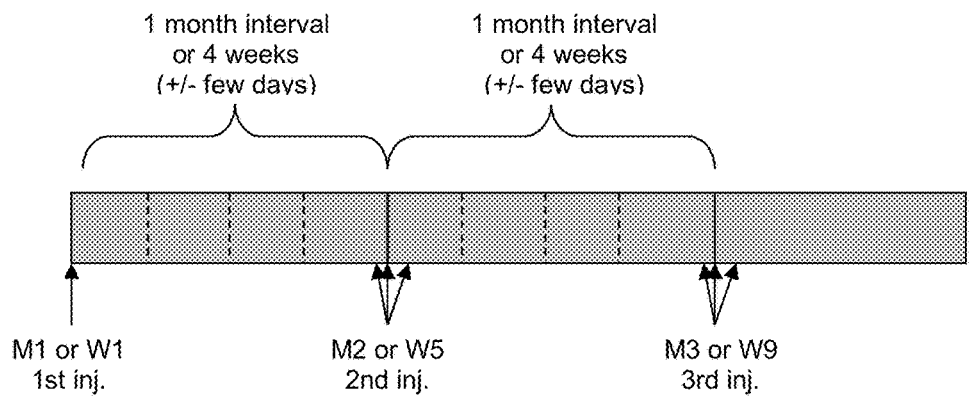

SEQ ID NO: 1: Amino acid sequence of the native human FGF-18.

SEQ ID NO: 2: Amino acid sequence of the recombinant truncated FGF-18 (trFGF-18).

SEQ ID NO: 3: Amino acid sequence of the recombinant human ilL-1 receptor antagonist (anakinra).

EXAMPLES

Material

The recombinant truncated FGF-18 (trFGF-18) of the present examples has been prepared by expression in *E. coli*, according to the technique described in WO2006/063362. In the following examples, trFGF-18 and FGF-18 are used interchangeably.

The recombinant human interleukin-1 receptor antagonist (anakinra) has been obtained via Pharmacia.

Scoring of Joints

After the sacrifice, the right knee was removed and decalcified in 5% formic acid for 4-6 d before cutting in half in the frontal plane and embedding in paraffin wax. Three sections were cut in 200 μm steps, stained with toluidine blue, and analyzed using ImagePro Plus™ software (Media Cybernetics). In scoring the three sections of the joint, the worst-case scenario for the two halves on each slide was determined for the cartilage lesion as the cartilage degeneration width (μm). This reflects the areas of tibial cartilage lesion in which both chondrocyte and proteoglycan loss extend 50% of the cartilage thickness. The measurement was taken over the area of greatest lesion severity in each of the three zones across the tibial surface.

A treatment group Mean±SE for each score and measurement was determined.

Data was analyzed using a one-way analysis of variance (1-way ANOVA) or Kruskal-Wallis test (non-parametric), along with an appropriate multiple comparison post-test. Right knee caliper measurements were compared to left using a Student's t-test. Unless indicated, Bolder BioPATH, Inc. performs statistical analysis on raw (untransformed) data only. Statistical tests make certain assumptions regarding the data's normality and homogeneity of variance, and further analysis may be required if testing resulted in violations of these assumptions. Significance for all tests was set at $p \leq 0.05$. Comparisons were made between each group and the vehicle control group, as well as between pairs

Example 1

Method:

The anterior cruciate ligament transection with resection of the medial meniscus (ACLT+tMx) model of instability-induced OA was performed in male Lewis rats 10-15 weeks of age. Briefly, under anesthesia with Isoflurane, the joint capsule of the right knee of each rat was opened, the anterior cruciate and the meniscus fixating ligaments were sharply transected, the meniscus was removed and the capsule, muscles and skin closed by sutures. Animals were randomly allocated into 10 groups of n=10 each. The following dosages were investigated: 0, 0.3, 1, 3 and 10 μg per intra-articular injection. Groups 1-5 received one cycle of three single injections at weekly intervals, group 6-10 three single injections at monthly intervals. Intra-articular treatment was started three weeks post-surgery. At this time pathophysiological changes are already mainifest, e.g., cartilage matrix loss. Animals were euthanized 17 weeks after surgery and joints were investigated.

Figure 2A:
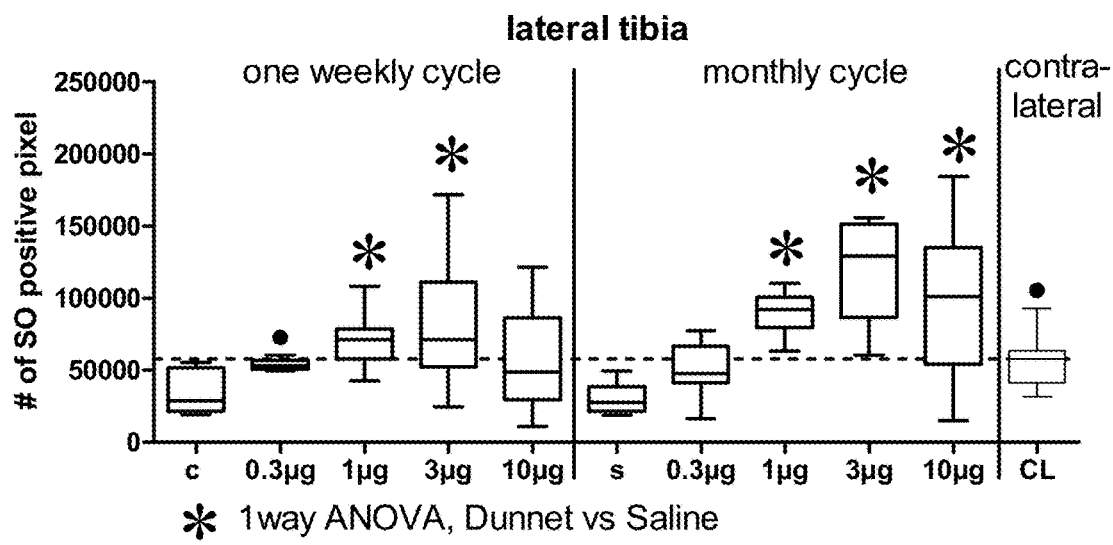
FIGS. 2A-2B: FGF-18 compounds evoke dose-dependent articular matrix deposition in a rat OA model illustrated by quantification of Safranin-O staining.
Figure 2B:
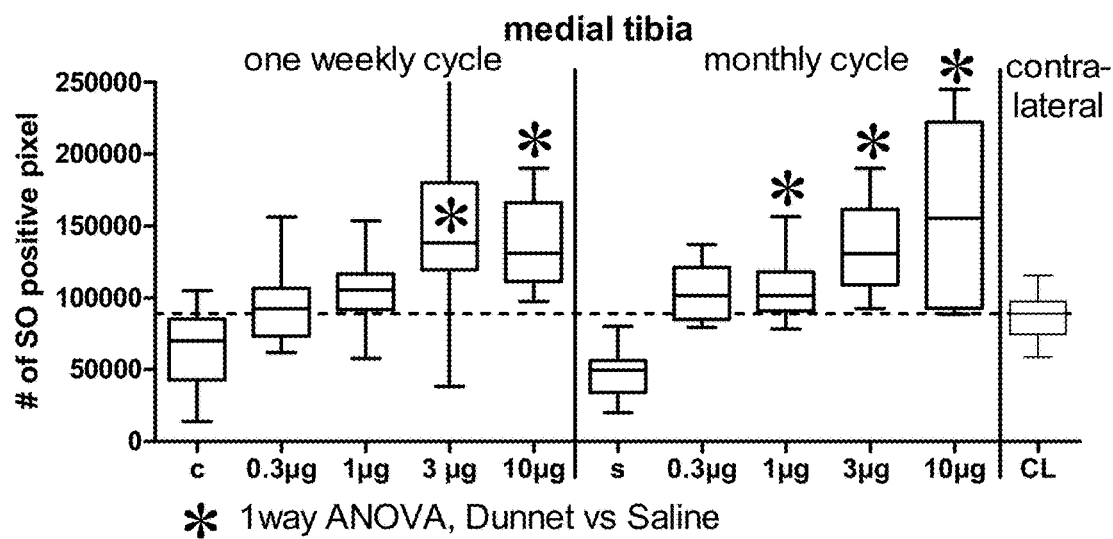

Results:

trFGF-18 induced dose-dependent neo-formation of cartilaginous tissue which became significant in the lateral tibia with 1 μg/joint independently of the injection regime (see FIG. 2a). trFGF-18 induced dose-dependent neo-formation of cartilaginous tissue which became significant in the medial tibia with 1 μg/joint according to the one-weekly regimen and with 0.3 μg/joint according to the one-monthly regimen (see FIG. 2b)

Example 2

Method:

Male Lewis rats underwent surgery (under anesthesia with Isoflurane) to induce a medial meniscal tear in the right knee joint. Animals were dosed IA with vehicle or FGF-18 on one of two different regimens (see table below), then terminated on day 105. Knees had caliper measurements taken at baseline and days 21, 42, 56, 84, and 105. Serum was evaluated for α2 macroglobulin levels at baseline and on days 21, and 105, as well as one week after the final dose (day 42 or 84). Right knees were collected for histopathology evaluation.

TABLE 1 treatment groups

| Group | Number of rats | Treatment (10 μg in 50 μl) |
|---|---|---|
| 1 | 10 | Normal + vehicle d 21, 35, 49 |
| 2 | 10 | surgery + vehicle d 21, 35, 49 |
| 3 | 10 | Surgery + FGF-18 d 21, 28, 35 (weekly treatment) |
| 4 | 10 | surgery + FGF-18 d 21, 35, 49 (bi-weekly treatment) |
| 5 | 10 | Surgery + FGF-18 d 21, 49, 77 (monthly treatment) |
| 6 | 10 | Surgery + FGF18 d 21, 35 |
| 7 | 10 | Surgery + FGF18 d 21, 77 |

Results and Conclusions:

All animals resumed weight bearing immediately post-surgery upon recovery from anesthesia. All animals gained weight over the course of the study and there were no significant differences in body weight change between groups.

Figure 3:
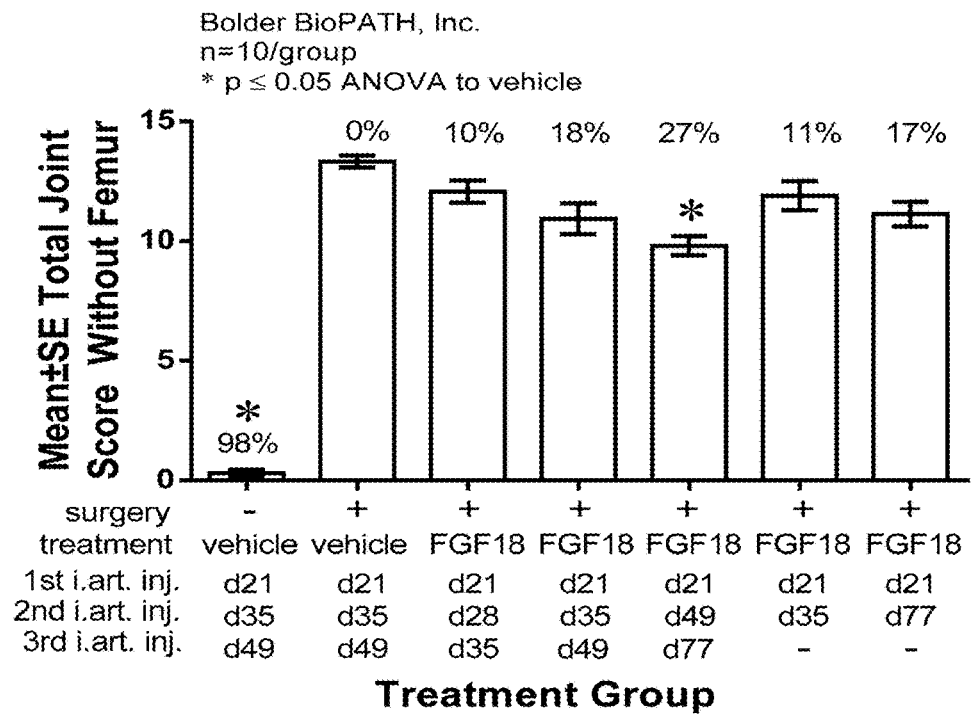
FIG. 3: Total Joint Score Without Femur.
Figure 4:
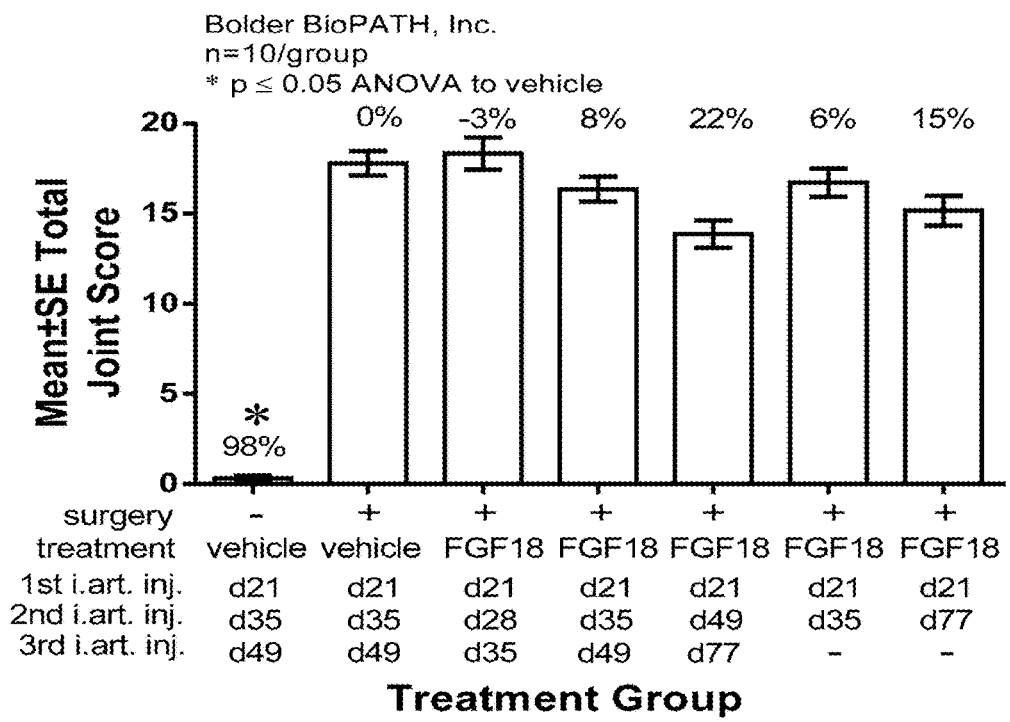
FIG. 4: Total Joint Score.
Figure 5:
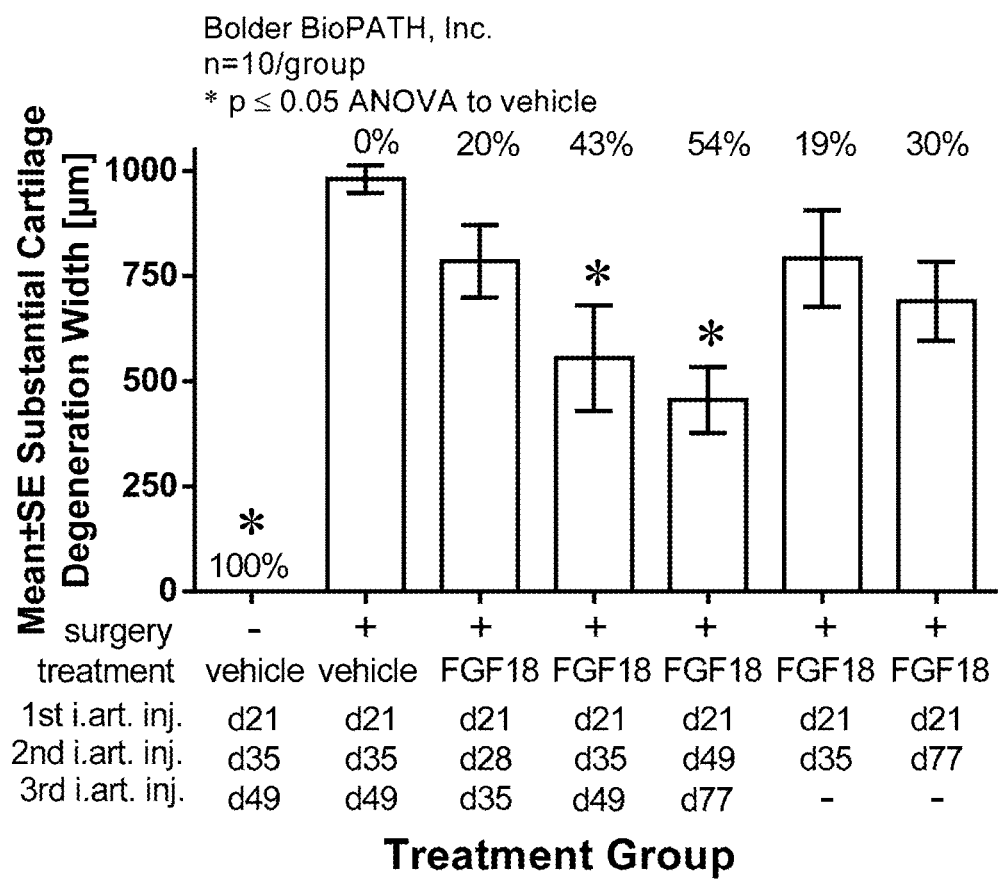
FIG. 5: Substantial Tibial Cartilage Degeneration Width.

Knee diameters, measured by caliper measurement and serum levels of a2MG, increased after FGF-18 injections but a clear benefit of one specific treatment regimen over another was not demonstrated in this study using these parameters. In contrast the structural benefit was highest with a monthly injection scheme (FIGS. 3, 4, 5).

Overall, results of this study indicate that treatment with FGF-18, regardless of regimen, significantly increased swelling in the treated knee after the first injection. Histopathology evaluation indicated that treatment generally increased the extent of injury over the tibial surface, particularly in terms of collagen damage, while reducing its severity. This effect was most evident in the treatment groups that received three doses rather than two, and in groups that received their final dose at the latest time point (day 77). Several other side effects of treatment were seen, including cartilage hypertrophy, synovitis, and synovial fibrosis. These changes were most evident and severe in animals that received three doses in rapid succession (Groups 3 and 4), while animals that received only two doses (Groups 6 and 7) or received their doses over a greater timeframe (Group 5) had slightly less severe changes.

The treatment regimen that resulted in the best overall morphology was the three injections, once monthly (Group 5; injections at days 21, 49, and 77), indicating that some recovery time between doses was beneficial.

Example 3

Methods:

60 adult male, naïve, New Zealand White rabbits were used for this study. Animals were approximately 3-4 months of age. Rabbits underwent surgery for creation of the cartilage defect right knee. A 2 mm by 6 mm full-thickness defect was made in the articular cartilage of the trochlear groove. The microfracture was created using 18 gauge needles. Two 3 mm deep microfractures were made through the subchondral bone at the base of the defect, one proximally and one distally. Each microfracture hole was approximately 1.5 mm in diameter and the holes separated by 2 mm.

The experiment consisted of the following six treatment groups, with 10 animals in each group for a total of 60 rabbits (Table 2). Rabbits in Groups 3, 4, 5 and 6 were treated with intra-articular rhFGF-18 in either one cycle of three weekly injections of 100 µg of rhFGF-18 (Group 3 and 5) or one cycle of three monthly injections of 100 µg of rhFGF-18 (Group 4 and 6). All animals were euthanized and necropsied 6 months after surgery.

injection of rhFGF-18 alone or in combination with microfracture, administered as a single weekly or monthly injection, resulted in thickening or enlargement of the femoral condyle region and a proliferation of rough or coarsely granular cartilage in the intercondylar groove lesion and stimulation of osteophytes on the medial and lateral trochlear ridges, occasional tibial plateau osteophyte formation, or abnormal cartilage growth on the patella or adjacent to the patella in the synovial fat pad.

With No Microfracture:

Right femur lesion sections from animals treated monthly for three months with rhFGF-18 had significantly increased defect fill percentages (48%), resulting in a significant 49% increase in the defect fill score. Other scores were non-significantly increased by 20-23%. The total width of the groove lesion was non-significantly increased by 36%, while the width of the lesion with no viable cartilage was significantly decreased by 94%. All sections had degeneration that ranged from minimal to severe, was generally focal, and was typically seen in conjunction with fibrocartilage. The central MFC thickness was significantly increased by 120%.

Morphological Pathology with Microfracture:

Sections of the cartilage lesion area from untreated controls with microfracture had overall moderate reconstitution of the osteochondral junction, moderately reduced matrix staining, and 50% fill of the defect. Cell morphology was mostly fibrocartilage.

Lesion area sections from animals treated weekly for three weeks with rhFGF-18 had significant 44-69% increases (toward normal) in all scored parameters, as well as the defect fill percent. Summed scores were significantly increased by 53%. The total width of the groove lesion was slightly increased by 5%, while the width of the lesion with no viable cartilage was decreased (non-significantly) by 59%. All sections had cartilage hypertrophy. Central MFC thickness in these sections was significantly increased by 112%.

TABLE 2 treatment groups

| Group # (n = 10) | Cartilage defect | Microfracture | Test article & treatment schedule | Dose µg/injection (trFGF-18) | trFGF-18 concentration (µg/ml) | Volume (ml/joint) | Day of dose |
|---|---|---|---|---|---|---|---|
| 1 | Yes | No | None | 0 | NA | NA | NA |
| 2 | Yes | Yes | None | 0 | NA | NA | NA |
| 3 | Yes | No | rhFGF18 (1×/week for 3 weeks | 100 | 500 | 0.2 | Day 7, 14, 21 |
| 4 | Yes | No | 1×/month for 3 months) | 100 | 500 | 0.2 | Day 28, 56, 84 |
| 5 | Yes | Yes | rhFGF18 (1×/week for 3 weeks | 100 | 500 | 0.2 | Day 7, 14, 21 |
| 6 | Yes | Yes | 1×/month for 3 months) | 100 | 500 | 0.2 | Day 28, 56, 84 |

Results:

Necropsy Findings (Table 3):

The ICRS gross cartilage score was 1.9+/−0.3 SE for Group 5 animals and 2.4+/−0.2 SE for Group 6 animals, indicating that the monthly injection scheme was superior compared to the weekly one. In Group 6 animals the intercondylar groove was filled in 3/10 animals with finely granular to granular cartilage; the remaining 7/10 animals had the groove 50% filled to nearly completely filled with granular to coarsely granular cartilage. In summary, the Lesion area sections from animals treated monthly for three months with rhFGF-18 had significant 61-97% increased (toward normal) in all scored parameters, as well as the defect fill percent. Summed scores were significantly increased by 76%. The total width of the groove lesion and the width of the lesion with no viable cartilage were non-significantly decreased by 19% and 69%, respectively. All sections had cartilage hypertrophy. Central MFC thickness in these sections was significantly increased by 106%.

Conclusions:

Abnormal clinical signs were mild and consistent with those typically seen in rabbits following knee surgery and/or as a result of repetitive sample collection, either blood collected from the lateral ear veins or synovial fluid collected from the knee joint. Comparison of intercondylar groove healing of animals in Group 1 and Group 2 showed good spontaneous filling of the groove with what grossly appears to be cartilage. There is a suggestion that microfracture may enhance cartilage regrowth in the groove since 9/10 animals in Group 2 had filling of the groove with cartilage compared to 7/10 animals in Group 1, but this difference is slight.

Likewise, there is no difference between ICRS or osteophyte scores between the two groups so the quality of cartilage healing was good, and there was little stimulation of osteophyte formation in either group. Of the remaining groups treated with rhFGF-18, it appears that Group 4 (intercondylar groove and three monthly intra-articular injections of 100 µg of rhFGF-18) showed the best response, with 6/9 animals having the intercondylar groove filled with cartilage that appeared nearly normal to slightly roughened or granular in gross appearance. In addition, Group 4 had the next to lowest ICRS cartilage score (2.1+/−0.3) of the four groups treated with rhFGF-18, and this group had the lowest osteophyte score (3.8+/−0.8) of any of the rhFGF-18 groups. In contrast, Group 6 (intercondylar groove with microfracture and three monthly intra-articular injections of 100 µg of rhFGF-18) had intercondylar groove filling in only 3/10 animals, the ICRS score was the highest of any group (2.4+/−0.2) and the osteophyte score was the second highest (5.1+/−0.7) of any rhFGF-18 treated group. Likewise, Group 5 (intercondylar groove with microfracture and three weekly intra-articular injections of 100 µg of rhFGF-18) had the highest osteophyte score of any group (5.7+/−0.7).

Beneficial effects were greater when treatment was given over an extended time period (3 months vs. 3 weeks), and effects were more evident in rabbits with microfractures than in rabbits without microfractures.

Example 4

Method:

Porcine chondrocytes were isolated from the cartilage of a femoral head of a pig hip (pigs were approximately one year old). After dissection of the joints, the cartilage was harvested and digested for 45 minutes with collagenase 0.25% (1/10 dilution of collagenase NBG4 2.5% in HAM's F12) at room temperature. The loosened cells were discarded and the cartilage further digested overnight with collagenase 0.1% (1/25 dilution of collagenase NBG4 2.5% in HAM's F12) at 37° C. to extract the chondrocytes. For this study, the chondrocytes were cultured in a monolayer.

Primary articular porcine chondrocytes were stimulated or not with 10 ng/mL IL1α and were either treated immediately or 6 hours later with anakinra 100 ng/mL and/or trFGF-18 100 ng/mL. Each condition was performed in 4 or 6-plicate. As a control, cells were also cultured with anakinra alone, trFGF-18 alone or in the absence of any treatment (medium).

Pre-culture: After cell isolation porcine chondrocytes were inoculated at 20,000 cells/cm$^2$ and cultivated for one week in complete HAM's F12. Cells were then harvested with accutase, counted and used as described below.

For cells treated directly with anakinra: Chondrocytes were inoculated in a 24-well plate at 15,000 cells/well in 0.5 mL of complete HAM's F12. Then 0.25 mL of trFGF-18 400 ng/mL and/or 0.25 mL of anakinra 400 ng/mL were added to the cells. In the challenged samples, 10 µL of IL1α at 1,000 ng/mL were also added to the cells. trFGF-18, anakinra and IL1α were all diluted in complete HAM's F12. The final volume in the culture well was adjusted to 1 mL with complete HAM's F12. Final concentrations were 10 ng/mL IL1α, 100 ng/mL trFGF-18 and 100 ng/mL anakinra and the total culture time was eight days. A complete medium change was performed after four days. N=4.

For cells treated with anakinra and trFGF-18 6 hours after the IL1α challenge: Chondrocytes were inoculated in a 24-well plate at 15,000 cells/well in 1 mL of complete HAM's F12 containing or not containing IL1α 10 ng/mL. After 6 hours the medium was removed and replaced with 0.25 mL trFGF-18 400 ng/mL and/or 0.25 mL of anakinra 400 ng/mL. In the challenged samples, 0.25 mL of IL1α at 40 ng/mL was also added to the cells. trFGF-18, anakinra and IL1α were all diluted in complete HAM's F12. The final volume in the culture well was adjusted to 1 mL with complete HAM's F12. Final concentrations were 10 ng/mL IL1α, 100 ng/mL trFGF-18 and 100 ng/mL anakinra and the total culture time was eight days. A complete medium change was performed after four days. N=6.

After eight days of culture, cells were harvested with accutase and resulting cell suspensions were analyzed for cell concentration and cell viability with a ViCell™ cell analyzer (from Beckman Coulter). Statistical analysis consisted of a 1-way ANOVA followed by a Dunnett post hoc analysis.

Figure 6A:
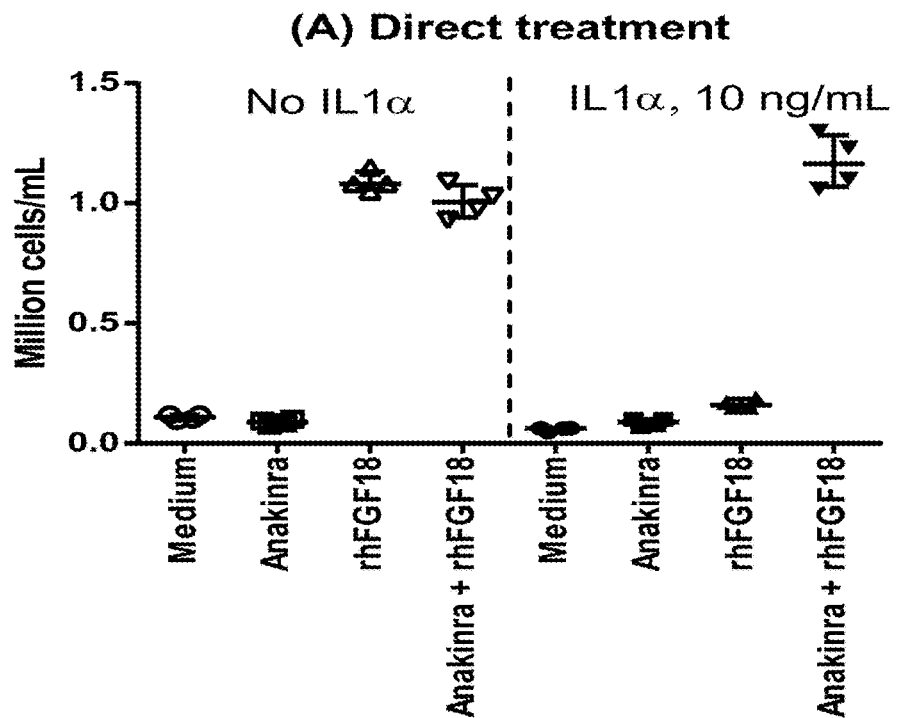
FIGS. 6A-6B: Cell concentration after 8 days of culture of porcine chondrocytes stimulated or not with IL1α and stimulated or not with IL1 days of culture (A) or after a 6-hour delay (B) with rhFGF-18 100 ng/mL and/or anakinra 100 ng/mL. N=4 for (A) and N=6 for (B).
Figure 6B:
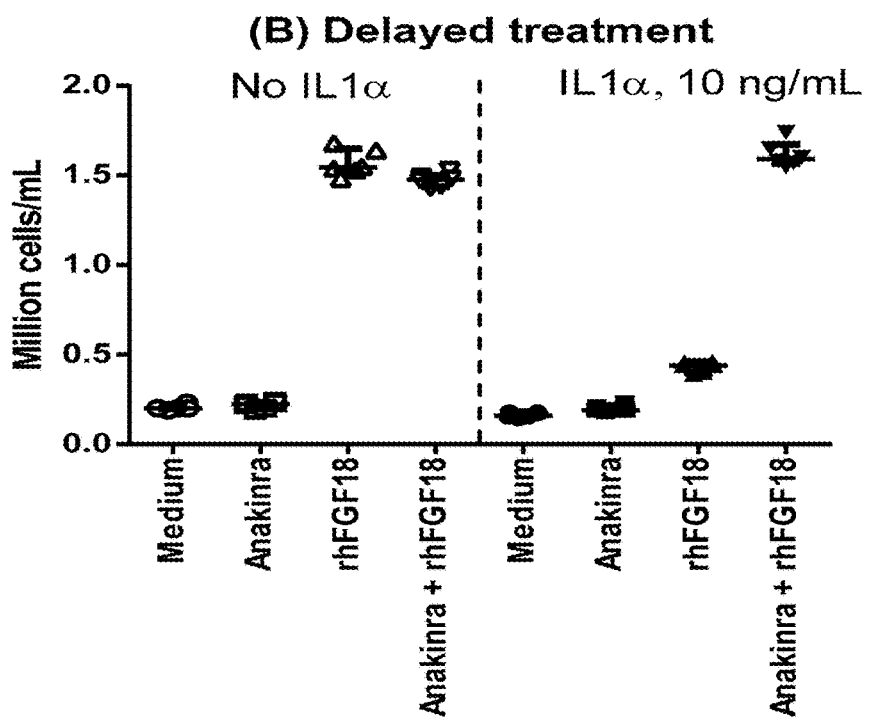

Results and Conclusions:

As expected, rhFGF-18 was found to increase porcine chondrocyte proliferation in the absence of IL1α. In both experiments in comparison with the control (medium, no IL1α) an 11.25 and 7.75-fold increase in the cell number was observed in the presence of rhFGF-18 100 ng/mL after 8 days of culture (FIG. 6). However, in the presence of IL1α 10 ng/mL, the stimulation of the proliferation by rhFGF-18 was only 2.38 and 2.44-fold, respectively, in comparison to the control (medium, IL1α, 10 ng/mL) for both experiments. Anakinra 100 ng/mL, for both the direct and the delayed treatments, was shown to fully restore rhFGF-18 activity. The cell density for cells cultured with rhFGF-18 and without IL1α or challenged with IL1α but treated with anakinra was found not to be statistically different. Finally, anakinra alone had no effect on chondrocyte proliferation.

In the present study, anakinra 100 ng/mL has been shown to fully block the inhibitory effect of IL1α on the proliferative activity of rhFGF-18. This in accordance with the fact that anakinra is an IL1 receptor antagonist, blocking the inflammatory signaling triggered by IL1. It has been presently demonstrated that anakinra restores the proliferative effect of rhFGF-18 in porcine chondrocytes challenged with IL1α.

Example 5

Method:

Male Lewis rats underwent surgery to induce a medial meniscal tear in the right knee joint. Animals were dosed i.a. with FGF-18 (10 µg/joint) on days 21, 28, and 35 and dosed orally with diclofenac (either 1 mg/kg or 3 mg/kg) or vehicle on days 21-23, 28-30, and 35-37, then terminated on day 42 or day 63. Serum was collected and evaluated for alpha 2 macroglobulin (α2MG) levels on days −3, 21, 42, and 63. α2MG is an inflammation serum biomarker. The link between α2MG and inflammation has already been shown (Kuribayashi et al., 2013).

Results

Figure 7:
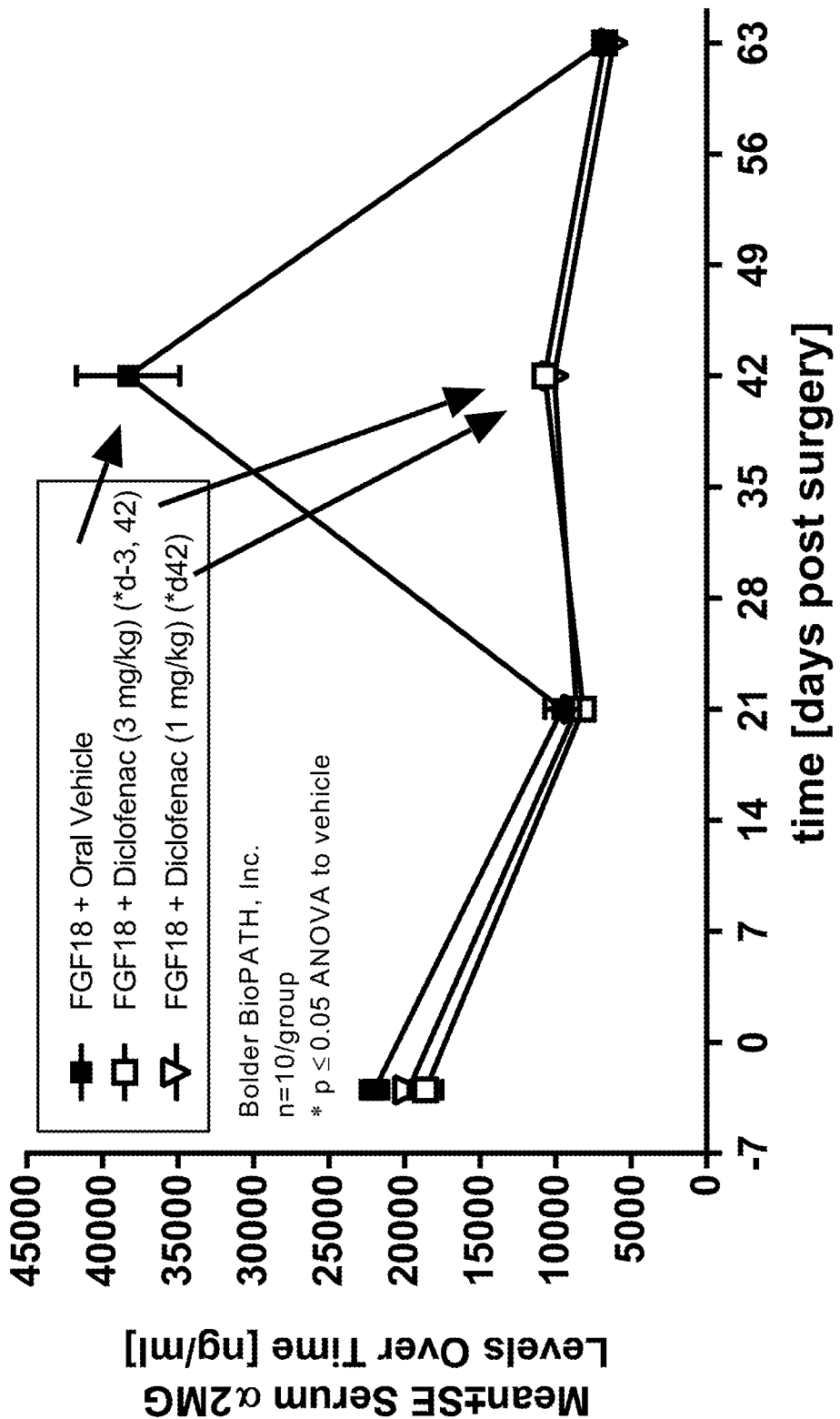
FIG. 7: Serum α2MG Levels Over Time.

FGF-18+vehicle controls had mild to moderate swelling on day 24, which increased to severe by day 36, although no limping was observed. Knee swelling diminished slightly to marked severity beginning on day 44. Caliper measurements supported these observations, with significant differences between right and left knees at day 21 and later time points, but not at the baseline. Animals given 3 mg/kg of diclofenac had significantly reduced swelling scores on days 24-29, 31, and 36-43, compared to the vehicle controls. Knee caliper measurements were significantly reduced on day 42, but were not significantly affected at any other time point. Animals given 1 mg/kg of diclofenac had significantly reduced swelling scores on days 24-29, 31, and 36-43, compared to the vehicle controls. Knee caliper measurements were significantly reduced on day 42, but were not significantly affected at any other time point (data not shown).

α2MG levels were higher on day −3 (pre-surgery) than at day 21 post-surgery. Levels in animals given 3 mg/kg of diclofenac were slightly but significantly reduced compared to those of the vehicle controls at the pre-surgery time point. Levels on day 21, prior to treatment, were essentially the same for all groups. On day 42, the disease controls had markedly elevated α2MG levels (approximately four times the day 21 levels), which was a significant difference from the two diclofenac groups. On day 63, levels for all groups were similar again (FIG. 7).

Conclusions:

Overall, results of this study indicate that administration of 1 or 3 mg/kg of diclofenac in rats with medial meniscal tears that were also given FGF-18 significantly reduced knee swelling, based on both clinical observations and caliper measurements. These effects were evident for approximately one week after the final dose of diclofenac. Serum levels of α2MG tracked with the vehicle controls on days −3, 21, and 63; however, a sharp reduction was seen on day 42 as a result of a massive spike in the control levels.

Example 6

Method:

The goal of this study was to evaluate the effect of different intracycle dosing frequency of the same total dosage (3×1 μg) of sprifermin on cartilage volume in a rat model of OA. The anterior cruciate ligament transection (ACLT) with resection of the medial meniscus (tMx) was performed as disclosed in Example 1. Joints from male Lister Hooded Rats (200-260 g, Charles River) were used in this study. Animals were euthanized 18 weeks post-surgery.

The changes in the joint are related to clinical assessments in OA (cartilage loss, osteophytes, subchondral sclerosis). One μg sprifermin in saline was injected three times either weekly, every 2nd, every 3rd, every 4th or every 5th week and compared to appropriate vehicle groups. Body weight, joint diameters and clinical health scores were investigated weekly.

Results

Results shown that intra-articular injections had no influence on the body weight gain. No significant drug or treatment regime effect was seen on the in-life parameter. However, groups injected every second week with saline (n=4) had the highest body weight gain tendency (data not shown).

Figure 8:
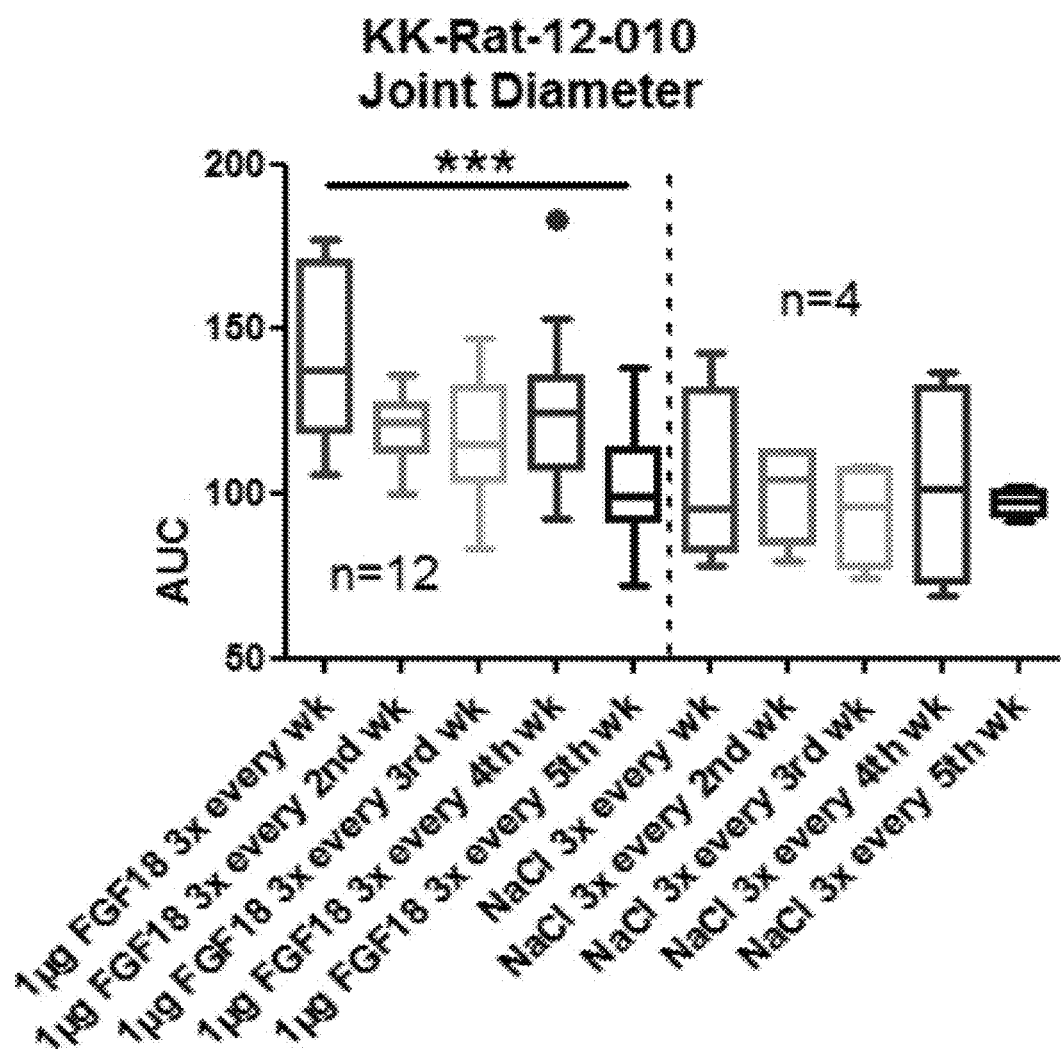
FIG. 8: AUC (area under the curve) of joint diameter difference between target knee (OA joint) and the contralateral joint (healthy knee) over time.

With injections in week 3, 4 and 5, joint diameters were significantly higher than after injections in week 3, 8 and 13 (see FIG. 8). No significant differences were seen between injections every 2nd, 3rd or 4th week. When injected only every 5th week AUC of joint diameters was the same as with saline injections. So, in tendency, the joint diameter AUC decreases with lower injection frequency.

Figure 9:
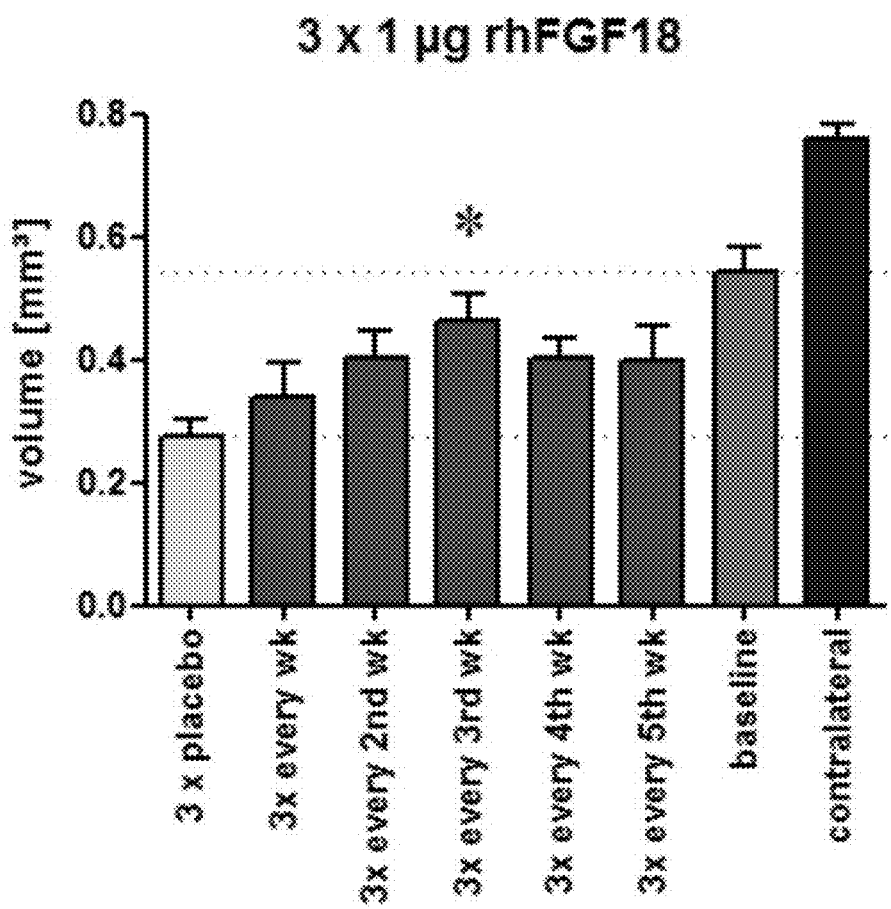
FIG. 9: cartilage volume (in $mm^3$) on medial tibia.

The quantitative histological analysis via stereology reviled severe OA-like changes in the affected joints. rhFGF-18 prevented more or less complete cartilage denudation. One μg/joint and injection given once every 3rd week (three injections in total) resulted in pharmacologically meaningful and statistically significant difference over saline (endpoint: cartilage volume on medial tibia, see FIG. 9).

Conclusions:

Lower injection frequencies than once weekly over three weeks seem to allow better recovery from joint swelling after injection. All groups treated with rhFGF-18 displayed structural benefits illustrated by higher cartilage volume values compared to placebo. However, under the circumstances of a time-fixed study (same study duration for all animals) and a fixed dosis, the injection frequency once every 3rd week resulted in the most beneficial structural outcome. It can be speculated that longer pauses between injections of rhFGF-18 are more beneficial because of better translation of chondrocyte proliferation into extracellular matrix production compared to the once weekly over three weeks injection regimen.

The resulting bell-shaped curve is a common observation for efficacy readouts of growth factors.

REFERENCES

1. Ellsworth et al., 2002, Osteoarthritis and Cartilage, 10: 308-320
2. Shimoaka et al., 2002, JBC, 277(9):7493-7500
3. WO2008/023063
4. WO2004/032849
5. WO98/16644
6. WO2006/063362
7. Custers et al., 2007, Osteoarthritis and Cartilage, 15:1241-1248
8. Lotz, 2010, Arthritis Research Therapy, 12:211
9. Moore et al., 2005, Osteoarthritis and Cartilage, 13:623-631
10. Arnaud-Dabernat et al., 2008, Journal of Cellular Physiology, 216:261-268
11. The Merck Manual, 17th Edition, 1999
12. Getgood et al., 2010, P116, ICRS Meeting 2010, Barcelona
13. ICRS publication: see Worldwide Website: cartilage.org/_files/contentmanagement/ICRS_evaluation.pdf, page 13
14. Bingham, 2002, J. Rheumatol., 29:3-9
15. Lee et al., 2013, Gene, 527:440-447
16. Bresnihan, 2002, Ann. Rheum., 61:ii74-ii77
17. St. Clair, 2002, J. Rheumatol., 29:22-26
18. Mertens et al., 2009, J. Rheumatol., 36(6):1118-1125
19. Chevalier et al., 2009, Arthritis & Rheumatism, 61(3): 344-352
20. Kuribayashi et al., 2013, Inflammation, 36(6):1448-52

The invention claimed is:

1. A method for the treatment of a cartilage disorder comprising administering to a subject having a cartilage disorder an FGF-18 compound selected from the group consisting of: a polypeptide comprising residues 28-207 of SEQ ID NO:1; and a polypeptide comprising SEQ ID NO:2, wherein said FGF-18 compound is administered at least twice per treatment cycle, said administrations being separated by about at least 3, 4 or 5 weeks.

2. The method according to claim 1, wherein said administrations are separated by about 3 weeks or by about 4 weeks.

3. The method according to claim 1, wherein said administrations are separated by about 1 month.

4. The method according to claim 1, wherein the FGF-18 compound is administered at least 3 times or at least 4 times per treatment cycle.

5. The method according to claim 1, wherein treatment cycles are repeated after 2, 3, 4, 5 or 6 months.

6. The method according to claim 1, which comprises 1, 2 or 3 treatment cycles per year.

7. The method according to claim 1, wherein the FGF-18 compound is administered intra-articularly.

8. The method according to claim 1, wherein the FGF-18 compound is administered at a dose of 3-300 mcg per single intra-articular administration.

9. The method according to claim 8, wherein the FGF-18 compound is to be administered at a dose selected from about 3, 10, 20, 30, 40, 50, 60, 90, 100, 120, 150, 180, 200, 240 or 300 mcg per single intra-articular administration of the FGF-18 compound.

10. The method according to claim 1, wherein the cartilage is articular cartilage.

11. The method according to claim 1, wherein the cartilage disorder is osteoarthritis.

12. The method according to claim 1, wherein the cartilage disorder is cartilage injury.

13. The method according to claim 1, wherein the FGF-18 compound is a polypeptide comprising residues 28-207 of SEQ ID NO:1.

14. The method according to claim 1, wherein the FGF-18 compound is administered together with an anti-inflammatory drug.

15. The method according to claim 14, wherein the anti-inflammatory drug is anakinra or diclofenac.

16. The method according to claim 14, wherein the anti-inflammatory drug is administered at a dose of 0.001-500 mg per single administration.

17. The method according to claim 16, wherein the anti-inflammatory drug is administered at a dose selected from 0.03, 0.1, 0.25, 0.3, 0.5, 1, 1.5, 2, 5, 10, 15, 20, 30, 40, 50, 60, 70, 80, 90, 100, 150, 200, 250 or 300 mg per single administration.

18. The method according to claim 1, wherein the FGF-18 compound is administered 3 times per treatment cycle, said administrations being separated by about 3 weeks.

19. The method according to claim 1, wherein the FGF-18 compound is administered 3 times per treatment cycle, said administrations being separated by about 4 weeks.

20. The method according to claim 1, wherein the FGF-18 compound is administered once monthly for 3 consecutive months.

21. The method according to claim 1, wherein the FGF-18 compound is a polypeptide comprising SEQ ID NO:2.

\* \* \* \* \*

SEQUENCE LISTING

<160> NUMBER OF SEQ ID NOS: 3

<210> SEQ ID NO 1
<211> LENGTH: 207
<212> TYPE: PRT
<213> ORGANISM: Homo sapiens
<220> FEATURE:
<223> OTHER INFORMATION: human FGF-18

<400> SEQUENCE: 1

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205

<210> SEQ ID NO 2
<211> LENGTH: 170
<212> TYPE: PRT
<213> ORGANISM: Artificial
<220> FEATURE:
<223> OTHER INFORMATION: Recombinant truncated FGF-18(trFGF-18)

<400> SEQUENCE: 2

Met Glu Glu Asn Val Asp Phe Arg Ile His Val Glu Asn Gln Thr Arg
1               5                   10                  15

Ala Arg Asp Asp Val Ser Arg Lys Gln Leu Arg Leu Tyr Gln Leu Tyr
            20                  25                  30

Ser Arg Thr Ser Gly Lys His Ile Gln Val Leu Gly Arg Arg Ile Ser
        35                  40                  45

Ala Arg Gly Glu Asp Gly Asp Lys Tyr Ala Gln Leu Leu Val Glu Thr
    50                  55                  60

Asp Thr Phe Gly Ser Gln Val Arg Ile Lys Gly Lys Glu Thr Glu Phe
65                  70                  75                  80

Tyr Leu Cys Met Asn Arg Lys Gly Lys Leu Val Gly Lys Pro Asp Gly
                85                  90                  95

```
Thr Ser Lys Glu Cys Val Phe Ile Glu Lys Val Leu Glu Asn Asn Tyr
            100                 105                 110

Thr Ala Leu Met Ser Ala Lys Tyr Ser Gly Trp Tyr Val Gly Phe Thr
            115                 120                 125

Lys Lys Gly Arg Pro Arg Lys Gly Pro Lys Thr Arg Glu Asn Gln Gln
            130                 135                 140

Asp Val His Phe Met Lys Arg Tyr Pro Lys Gly Gln Pro Glu Leu Gln
145                 150                 155                 160

Lys Pro Phe Lys Tyr Thr Thr Val Thr Lys
                165                 170

<210> SEQ ID NO 3
<211> LENGTH: 153
<212> TYPE: PRT
<213> ORGANISM: Artificial
<220> FEATURE:
<223> OTHER INFORMATION: Recombinant human interleukin-1 receptor
      antagonist (anakinra)

<400> SEQUENCE: 3

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
                20                  25                  30

Ala Gly Tyr Leu Gln Gly Pro Asn Val Asn Leu Glu Glu Lys Ile Asp
            35                  40                  45

Val Val Pro Ile Glu Pro His Ala Leu Phe Leu Gly Ile His Gly Gly
        50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
            115                 120                 125

Asp Gln Pro Val Ser Leu Thr Asn Met Pro Asp Glu Gly Val Met Val
            130                 135                 140

Thr Lys Phe Tyr Phe Gln Glu Asp Glu
145                 150
```